(12) United States Patent
Davis et al.

(10) Patent No.: US 7,036,454 B2
(45) Date of Patent: May 2, 2006

(54) INSECT HOLDER

(75) Inventors: Paul James Davis, Bedford (GB);
Peter William Tomkins, Hertfordshire (GB); Kenneth Alan Cherry, Bedford (GB); Justin Sheldon Bayliss, Worcester (GB)

(73) Assignee: Inscentinal Limited, London (GB)

( * ) Notice: Subject to any disclaimer, the term of this patent is extended or adjusted under 35 U.S.C. 154(b) by 0 days.

(21) Appl. No.: 10/497,605

(22) PCT Filed: Dec. 20, 2002

(86) PCT No.: PCT/GB02/05880

§ 371 (c)(1),
(2), (4) Date: Jun. 3, 2004

(87) PCT Pub. No.: WO03/055301

PCT Pub. Date: Jul. 10, 2003

(65) Prior Publication Data

US 2005/0103276 A1 May 19, 2005

(30) Foreign Application Priority Data

Dec. 22, 2001 (EP) .................................. 01310854

(51) Int. Cl.
*A01K 29/00* (2006.01)
*A01K 47/06* (2006.01)
*A01M 5/00* (2006.01)

(52) U.S. Cl. ........................ 119/6.5; 119/417; 119/751; 43/133; 449/27

(58) Field of Classification Search ................ 119/6.5, 119/417, 416, 421, 751; 43/132.1, 133, 134, 43/136; 206/15.3; 449/6, 2, 3, 27; 436/63; 422/98; 435/4, 287.1; 424/9.1; 73/866

See application file for complete search history.

(56) References Cited

U.S. PATENT DOCUMENTS

| 2,093,784 A | | 9/1937 | Southwick |
| 2,655,968 A | * | 10/1953 | Simmons ..................... 15/247 |
| 3,746,162 A | * | 7/1973 | Bridges ....................... 206/361 |
| 4,022,054 A | * | 5/1977 | Biederman ................. 73/23.34 |
| 4,218,842 A | * | 8/1980 | Anderson .................... 43/122 |
| 4,227,333 A | * | 10/1980 | Levinson et al. ............ 43/107 |
| 5,090,153 A | * | 2/1992 | Mullen et al. ............... 43/114 |
| 5,134,892 A | * | 8/1992 | Wilson et al. ............... 73/866 |
| 5,158,497 A | | 10/1992 | Rossignol et al. |
| 5,320,069 A | * | 6/1994 | Anderson et al. .......... 119/751 |

(Continued)

FOREIGN PATENT DOCUMENTS

AT  397 755 B  6/1994

(Continued)

*Primary Examiner*—Yvonne R. Abbott
(74) *Attorney, Agent, or Firm*—Morgan Lewis & Bockius LLP

(57) ABSTRACT

An insect holder for holding an insect, e.g. a forager honey bee, comprises a housing with a chamber adapted to receive the insect, an inlet to the chamber through which the insect can pass to enter the chamber, and a head opening to the chamber adapted to permit the head of the insect in the chamber to pass therethrough to the exterior of the housing while retaining the insect in the housing, with the head of the insect protruding through the head opening to the exterior of the housing. The insect is constrained to be unable to turn around in the chamber or withdraw its head into the chamber, so that observations can be made on the insect head, e.g. monitoring proboscis movement in known manner. When observations are finished, the insect is released unharmed and undamaged.

18 Claims, 8 Drawing Sheets

U.S. PATENT DOCUMENTS

| | | | |
|---|---|---|---|
| 5,779,046 A * | 7/1998 | Plakos | 206/362.3 |
| 5,924,567 A * | 7/1999 | Wenum | 206/362.3 |
| 5,927,234 A * | 7/1999 | Siegel | 119/751 |
| 2001/0029900 A1* | 10/2001 | Weber | 119/453 |
| 2001/0047612 A1* | 12/2001 | Prince | 43/58 |
| 2003/0148529 A1* | 8/2003 | Lewis et al. | 436/63 |

FOREIGN PATENT DOCUMENTS

| | | |
|---|---|---|
| DE | 195 36 389 A | 4/1997 |
| JP | 61083964 A * | 4/1986 |

* cited by examiner

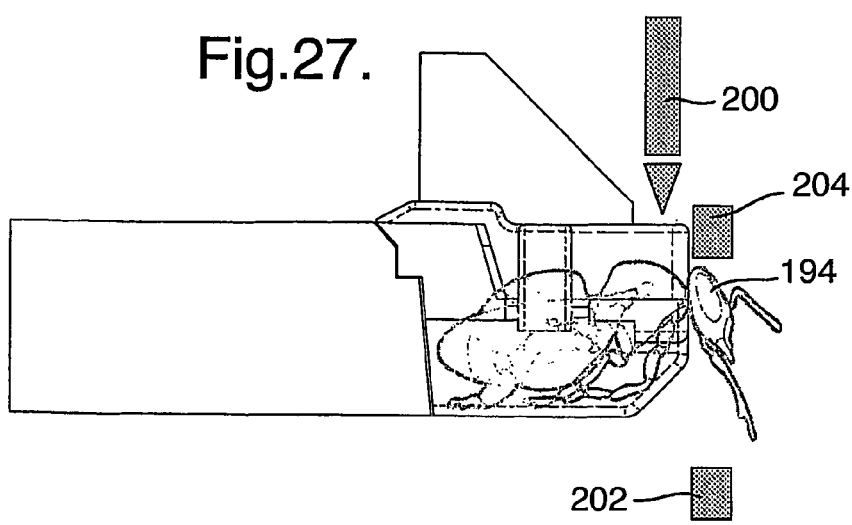
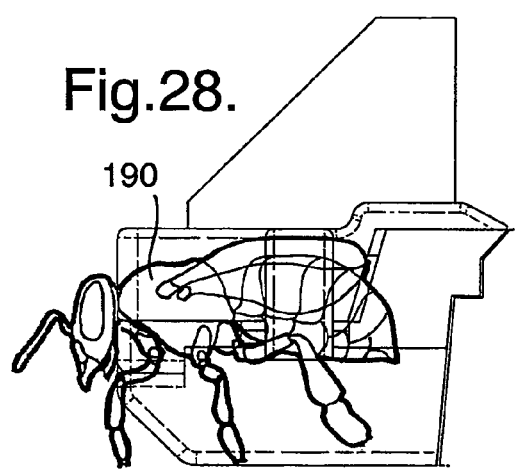
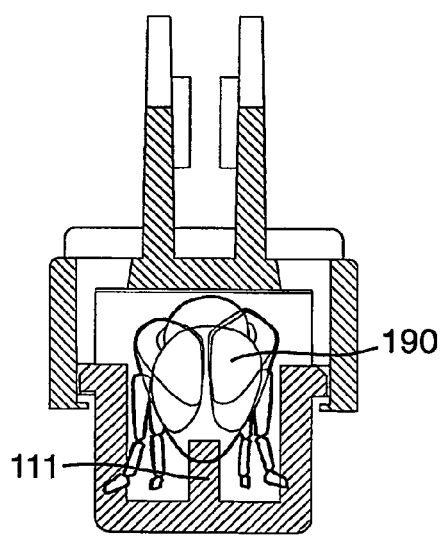
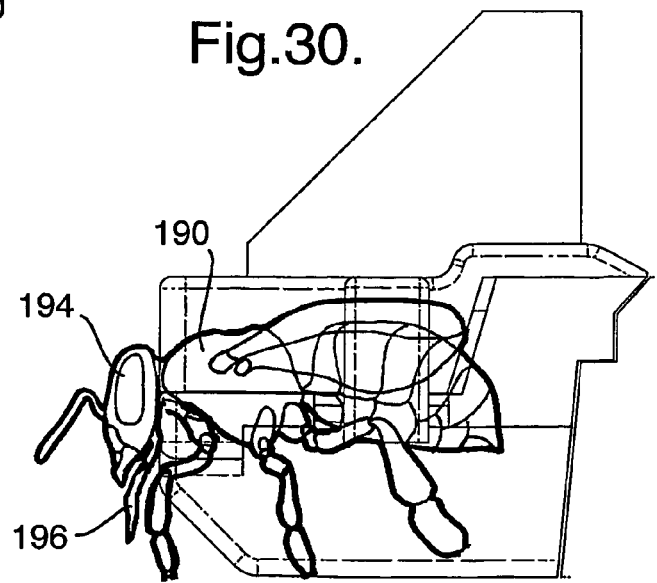

INSECT HOLDER

FIELD OF THE INVENTION

This invention relates to an insect holder for holding an insect such as a bee, e.g. for research purposes.

BACKGROUND TO THE INVENTION

When performing research into aspects of the behaviour of bees, it is known to restrain bees in individual holders, e.g. to enable monitoring of reflex proboscis extension responses following stimulation. In general, the known bee holders comprise a cylindrical tube cut away in part to provide a semi-cylindrical portion into which a bee is located, with the bee being held in position by the use of one or more strips of adhesive tape, passing across or behind the head, and/or around the thorax of the bee. See, for example, Batson et al, Journal of Comparative Psychology, 1992, Vol 106, No 2, 114–119; Shafir et al, Animal Behaviour, 1999, 57, 1055–1061; Buckbee et al, Journal of Insect Behaviour, Vol 10, No 4, 1997, 479–491 and Abramson et al, J Entomol. Sci. Vol 36, No 1 (2001).

The bees are generally exposed to a reduced temperature immediately prior to location in a holder to reduce the activity of the bees and make them easier to handle. Nevertheless, locating and securing a bee in a holder is a skilled task. Further, the use of adhesive tape to restrain the bees in position is liable to damage the bees.

The present invention aims to provide an alternative insect holder that is less likely to damage insects held therein.

SUMMARY OF THE INVENTION

According to the present invention there is provided an insect holder for holding an insect of a particular type, the holder comprising a housing with a chamber adapted to receive an insect of the particular type, an inlet to the chamber through which an insect of the particular type can pass to enter the chamber, a head opening to the chamber adapted to permit the head of an insect of the particular type in the chamber to pass therethrough to the exterior of the housing while retaining the insect in the housing, and retaining means for retaining an insect of the particular type in the chamber with the head of the insect protruding through the head opening to the exterior of the housing, such that the insect is unable to turn around in the chamber.

In use, an insect of the particular type enters the chamber via the inlet, and is then retained in the holder by the retaining means. The insect is retained in the chamber, with its head protruding through the head opening of the chamber. The insect is constrained to be unable to turn around in the chamber or withdraw its head into the chamber, so the head of the insect must remain outside the chamber. The insect is thus held in the holder with the head visible, so that observations can be made on the insect head, e.g. monitoring proboscis extension in known manner, for instance as disclosed in the papers referred to above. When observations are finished, the retaining means can be removed or deactivated so that the insect is able to leave the chamber, with the insect unharmed and undamaged. The chamber is thus adapted to receive an insect in removable manner, such that an insect that has been held in the holder can be removed therefrom unharmed and undamaged.

The insect can be made to enter the chamber in a number of different ways, including the following:

1. The insect may be lured to enter the chamber by use of one or more attractants, e.g. food, odour, light etc., (e.g. a sugar solution to attract bees), suitably positioned downstream of the chamber.
2. The insect may be manually put into the chamber by a skilled handler.
3. The insect may be blown into the chamber by a suitably directed stream of gas, e.g. air.

The insect holder of the invention is applicable to use with a range of different insects, with a particular holder being designed and dimensioned to hold an insect of a particular type, e.g. a particular species. For example, the invention finds particular application in a holder for forager honey bees (species *Apis mellifera*). In this case, the chamber suitably has a width of at least 5 mm and a length of about 13 mm, with the head opening being about 4 mm in diameter.

The retaining means may be in the form of closure means for closing the inlet, to prevent the insect leaving the chamber via the inlet. The closure means may comprise a member, e.g. a plug, adapted to be removably fitted into the inlet. When observations have been completed, the closure means can be removed, opening the chamber inlet so that the insect is able to leave the chamber via the inlet.

The retaining means may alternatively or additionally be in the form of a collar or barb locatable between the head and thorax, between the thorax and abdomen or behind the abdomen of an insect in the chamber. Such a collar or barb may be in the form of a one-way gate or valve arrangement, e.g. being suitably shaped (for instance ramped) or biassed to permit an insect to enter the chamber but not to leave. Alternatively or additionally such a collar or barb may be movable between an open position, in which movement of the insect into the chamber is permitted, and a closed or latched position, in which movement of the insect from the chamber is prevented. Activation means may be provided for moving the collar or barb, possibly automatically in response to correct positioning of an insect in the holder.

The head opening may be of circular form, but is preferably non-circular, e.g. part circular, and designed to prevent an insect in the holder from curling its head towards the chamber. The head opening may have a slit extending therefrom, positioned to facilitate certain insect movements such as proboscis extension.

The head opening may optionally have a head restraint associated therewith, to limit head movements of an insect in the holder.

In a simple embodiment the chamber is of generally circular cylindrical form. Preferably, however, the chamber is of non-circular internal cross-sectional form and is instead shaped and configured to prevent an insect held therein from wriggling and turning around. To this end the chamber desirably has an internal longitudinal projection or rib running along at least part of the length thereof on which the underside of body parts of an insect can rest, with a respective longitudinal channel on each side of the projection or rib into which the legs of an insect can fit, possibly gripping the sides of the projection or rib. Such an arrangement helps to orient the insect in a desired position.

It may similarly be advantageous for the chamber to include apertures constituting leg holes through which the legs of an insect in the holder can pass, again to assist in orientation of the insect.

In a simple embodiment, the housing is of generally circular-section tubular form, defining a chamber of generally circular cylindrical form. The cylindrical chamber is open at both ends, with the opening at one end constituting the inlet and a reduced size opening at the other end constituting the head opening. The retaining means comprises closure means for closing the inlet, typically comprising a member such as a plug, adapted to be removably fitted into the inlet. In the case of an embodiment of this form for use in holding a forager honey bee, the chamber is 5 mm in diameter, with the inlet opening being at least as big, and the head opening is 4 mm in diameter. The length of the chamber when the inlet is closed by the closure means is 13 mm. A holder of such dimensions functions to restrain a forager honey bee in the chamber with the head protruding though the head opening, and with the bee being prevented from turning around within the chamber. The head opening may be of circular form but is preferably part circular, e.g. approximately semi-circular, to prevent the bee from curling its head towards the chamber.

The housing is conveniently made of rigid plastics material, e.g. acetal, acrylic, polypropylene, Nylon (Nylon is a Trade Mark) etc, and may be made by any convenient technique e.g. machining, moulding etc.

In a further aspect the present invention provides an insect holder in accordance with the invention with an insect, particularly a bee, held therein.

In another aspect the invention provides odour sensing apparatus comprising an insect holder in accordance with the invention with an insect, particularly a bee, held therein; and means for detecting a response of the insect in the holder to an odour.

The detecting means conveniently comprise suitable image analysis equipment, such as a CCD camera.

Embodiments of the invention in the form of holders for a forager honey bee will now be described, by way of illustration, with reference to the accompanying drawings in which:

FIG. 27 is a schematic side view of the bee holder shown in FIGS. 16 to 26, with means for closing the holder;

FIG. 28 is a schematic longitudinal section view illustrating a bee in the bee holder of FIGS. 16 to 27, with the holder in the second, closed position;

FIG. 29 is a schematic transverse sectional view illustrating a bee in the bee holder of FIGS. 16 to 28, with the holder in the second, closed position; and FIG. 30 is a view similar to FIG. 28, from the other side, with the proboscis of the bee extended.

DETAILED DESCRIPTION OF THE DRAWINGS

Figure 1:
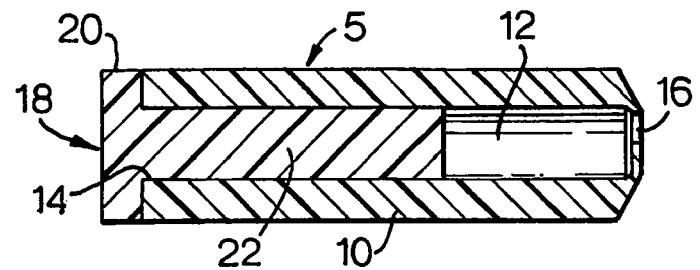
FIG. 1 is a longitudinal section of one embodiment of a bee holder in accordance with the invention.
Figure 2:
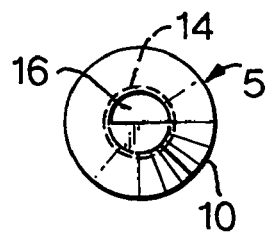
FIG. 2 is a front view of the holder of FIG. 1, seen from the right hand side.

Referring to the drawings FIGS. 1 and 2 show a simple embodiment of a bee holder 5 comprising a generally tubular circular section housing 10 of acetal plastics material, defining a circular cylindrical chamber 12. Housing 10 has a length of 33 mm and a diameter of 10 mm. Chamber 12 has a diameter of 5 mm. Opening 14 at one end of the housing constitutes a 5 mm diameter circular inlet to the chamber. Opening 16 at the other end of the chamber is 4 mm in diameter, and of semi-circular form, and constitutes a head opening to the chamber. The housing surrounding opening 16 is bevelled at an angle of 28°.

Housing 10 was made by machining a 10 mm diameter rod of acetal.

A removable plug 18 comprising a circular end cap 20 and rod portion 22 is shown in position, closing inlet 14 and constituting retaining means. Rod portion 22 is 20 mm long, so with the plug in position the chamber 12 is 13 mm long.

In use a forager honey bee is inserted into the chamber 12 through inlet 14, head first. For example, a skilled handler can pick up a bee by its wings and manually insert the bee into the holder. The bee may then be blown along the chamber by a stream of gas, e.g. air, directed into inlet 14 (for instance by the handler gently blowing into inlet 14), to move the bee to the other end of the chamber with its head protruding through opening 16. Plug 18 is then fitted into inlet 14 to retain the bee in the holder. The length and diameter of the chamber and the size of the opening 16 are such that the bee is retained and restrained in the chamber with its head protruding through opening 16 to the exterior of the housing. The opening 16 is dimensional to permit the head but not the body of the bee to pass therethrough so the body of the bee is retained in the chamber. The chamber is dimensioned to prevent the bee turning around or withdrawing its head into the chamber.

Figure 3:
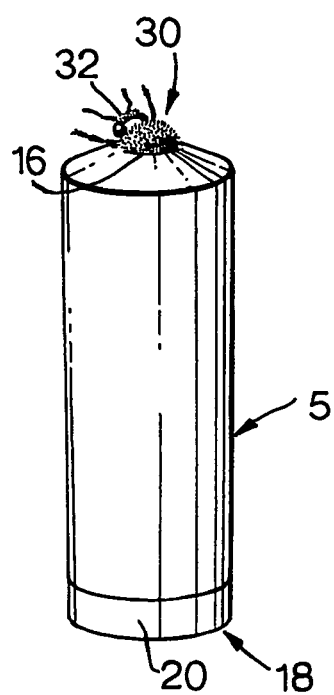
FIG. 3 is a perspective view of the holder of FIGS. 1 and 2 with a forager honey bee held therein.

FIG. 3 shows the holder 5 of FIGS. 1 and 2 with a bee 30 held therein, with the head 32 of the bee visible protruding through opening 16.

With the bee restrained in the holder, observations of the head can be made, e.g. proboscis extension may be monitored, e.g. for research purposes. When observations have finished, the plug 18 may be removed and the bee allowed to exit the holder via inlet 14, with the bee in undamaged and unharmed condition.

Figure 4:
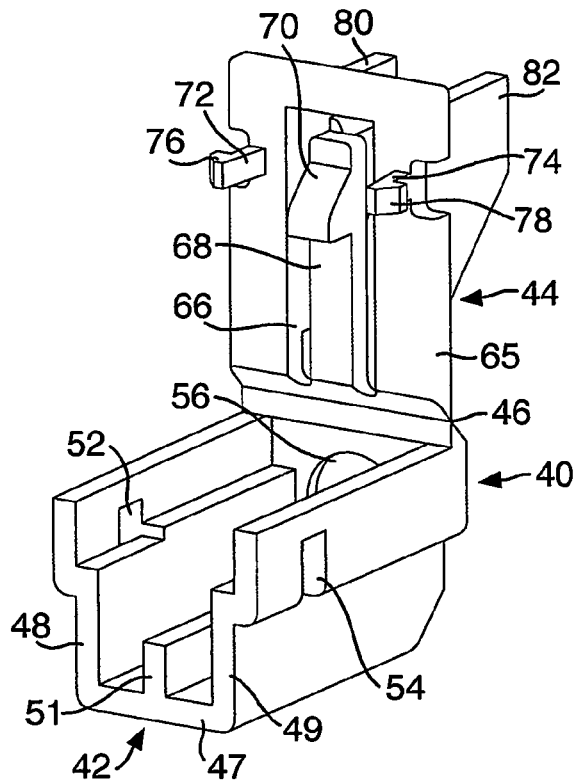
FIG. 4 is a view from the rear and one side (the right side) of a moulding for a second embodiment of bee holder in accordance with the invention.
Figure 5:
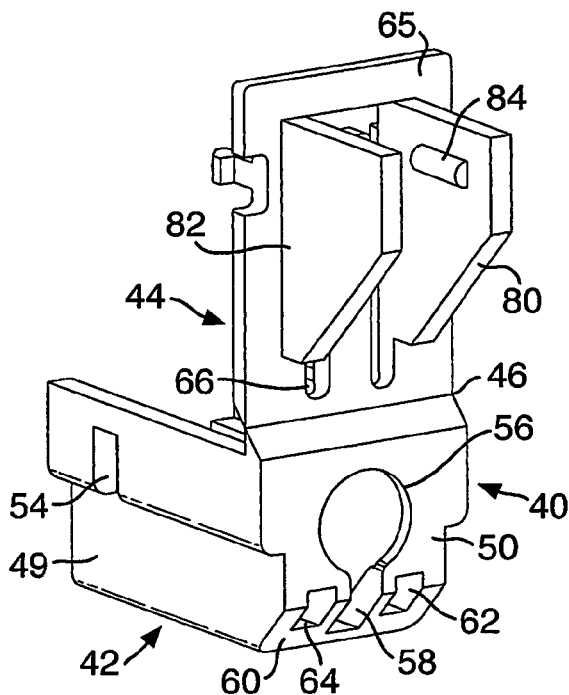
FIG. 5 is a view from the front and right side of the bee holder moulding shown in FIG. 4.
Figure 7:
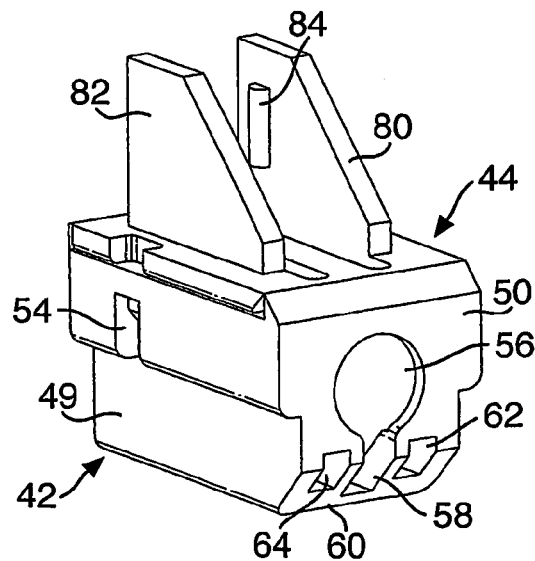
FIG. 7 is a view from the front and right side of a bee holder formed from the moulding shown in FIGS. 4 to 6.
Figure 6:
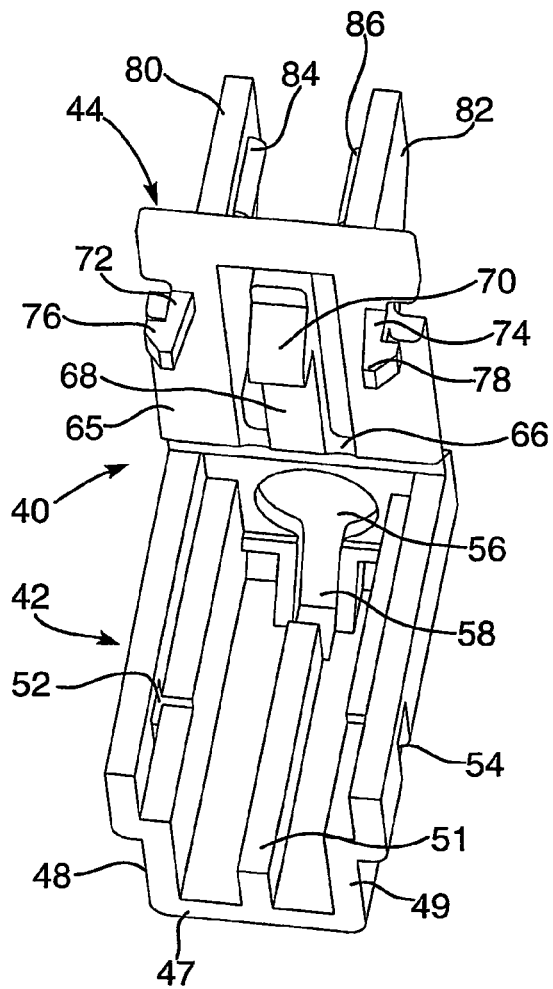
FIG. 6 is a view from the rear and above of the bee holder moulding shown in FIGS. 4 and 5.
Figure 8:
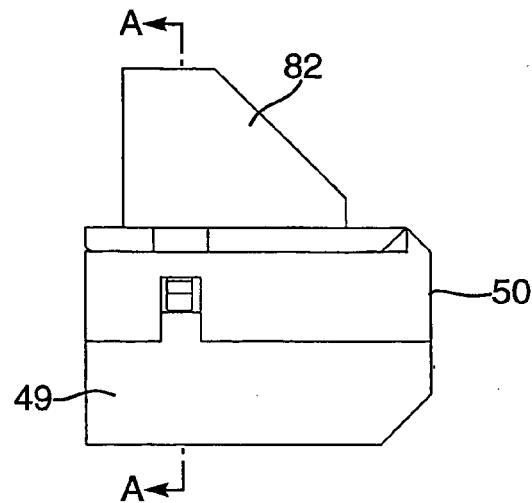
FIG. 8 is a view from the right side of the bee holder shown in FIG. 7.

FIGS. 4 to 14 illustrate a further embodiment of bee holder made from a one piece polypropylene moulding 40, as shown in FIGS. 4 to 6, manufactured using an open and shut injection moulding tool. The moulding comprises a lower channel portion 42 and an upper lid portion 44 connected by a thin web 46 (shown schematically in the drawings) that constitutes an integral hinge.

The lower channel portion 42 includes a bottom wall 47, side walls 48 and 49 and a front wall 50. The rear of the lower channel portion is open. A longitudinal rib 51 extends upwardly from the bottom wall 47. The side walls 48 and 49 are each of stepped configuration and include a respective opening 52, 54 for closure purposes, to be discussed below. The front wall has a circular opening 56 therein, with a central slit 58 extending downwardly therefrom and terminating in a lower inclined portion 60 of the front wall. A respective rectangular opening, 62, 64 is provided in the front wall, on each side of the slit 58.

The upper lid portion 44 includes a generally planar cover member 65, with a central opening 66 in which is located a tongue 68 having a barb 70 adjacent the free end thereof for trapping and retaining a bee in the holder, as will be discussed below, thus constituting retaining means. A pair of arms 72, 74 extend perpendicularly from the underside of the lid portion 44, each terminating in a respective outwardly directed flange portion 76, 78 for engaging in the openings 52, 54 for closure purposes. A pair of generally triangular fins or mounting clips 80, 82 extend perpendicularly from the upper side of the lid portion 44, with a respective location rib 84, 86 on the adjacent inner faces of the clips.

Figure 9:
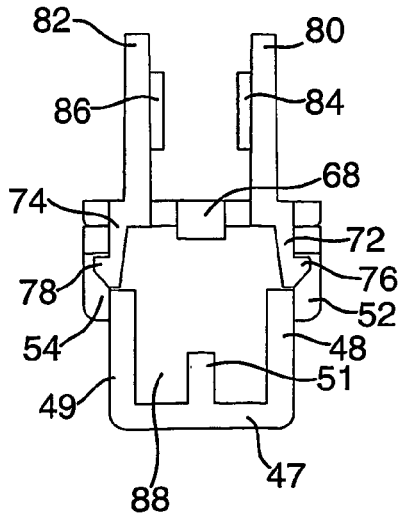
FIG. 9 is a sectional view along line A—A in FIG. 8.

The bee holder is produced from the moulding 40 by pivoting the portions 42 and 44 towards each other, around hinge 46, so that the lid portion 44 overlays the channel portion 42 as shown in FIGS. 7 to 14. FIGS. 11 to 14 include a schematic representation of a bee in the holder. The arms 72, 74 are sufficiently resiliently deformable to enable the flange portions 76, 78 to move within the lower channel portion yet engage in the openings 52, 54, thus locking the lid portion 44 into position on the lower channel portion with a snap fit (FIG. 9). The resulting bee holder is of generally box-like form, having an overall length of 14 mm, an overall height of 9 mm (excluding the upstanding mounting clips), a maximum width of 9 mm, with a narrower lower portion 7 mm wide. The holder defines a generally box-like chamber 88, having a width in the lower portion of 5 mm. The clearance between the top of the rib 51 and the underside of the cover member 65 (and tongue 68) is 5 mm, with the spacing between the top of the rib 51 and the barb 70 being 3.5 mm. The rib 51 is 1.8 mm wide. The open rear of the lower channel portion constitutes an inlet to the chamber, and the circular opening 56 (which has a diameter of 4 mm) in the front wall constitutes a head opening for a bee located in the chamber.

Figure 10:
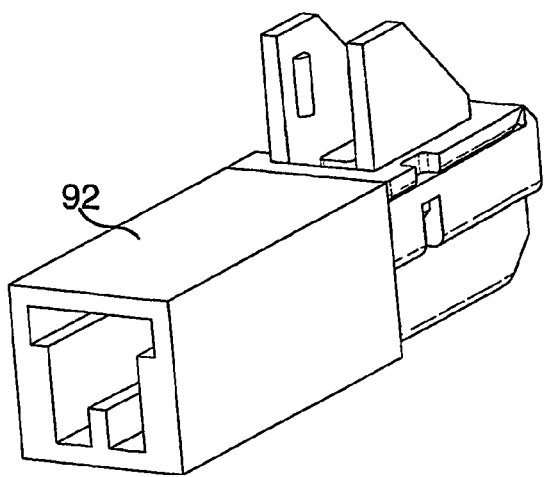
FIG. 10 is a view from the rear and right side of the bee holder shown in FIGS. 7 to 9 with an attached loading tunnel.
Figure 11:
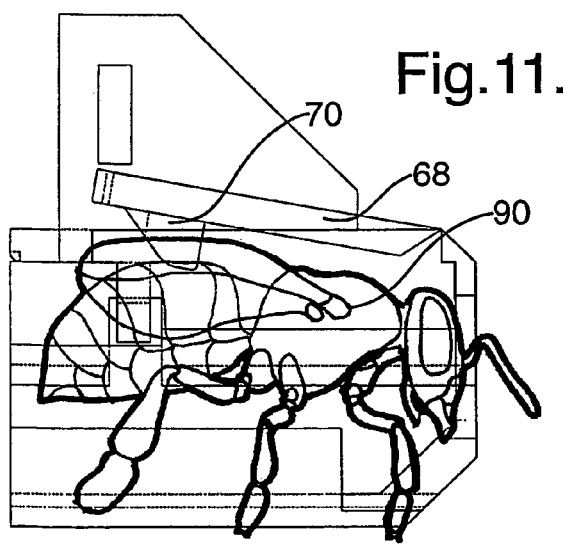
FIG. 11 is a schematic longitudinal sectional view illustrating a bee entering the bee holder shown in FIGS. 7 to 10.
Figure 12:
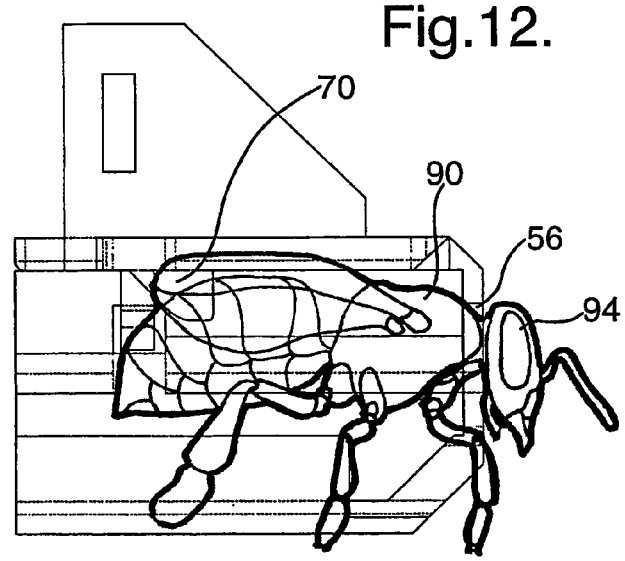
FIG. 12 is a view similar to FIG. 11 showing a bee fully located in the bee holder.
Figure 13:
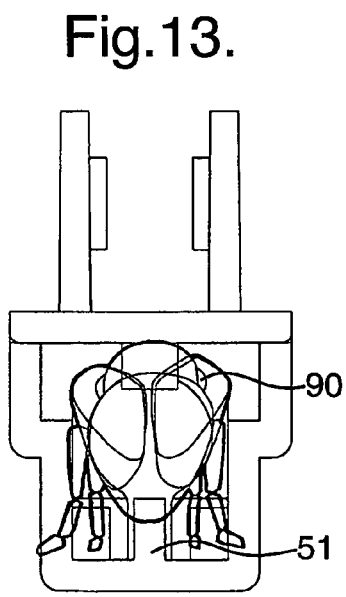
FIG. 13 is a front view illustrating a bee in the holder shown in FIGS. 7 to 12.

In use, a forager honey bee 90 is inserted into the chamber 88 through the inlet constituted by the open rear of the lower channel portion, head first. The bee may be inserted manually by a skilled handler. Alternatively the bee may be lured to enter the chamber by use of one or more attractants suitably positioned downstream of the chamber. The bee may enter the chamber via a loading tunnel, of similar internal cross-sectional form to the chamber, as shown in FIG. 10. As the bee enters the chamber, the tongue 68 is moved upwardly, as shown in FIG. 11, on engagement of barb 70 with the back of the abdomen of the bee. When the bee has fully entered the chamber, with the head 94 of the bee protruding through the opening 56, as shown in FIG. 12, the tongue resumes its original position due to the resilient nature of the material, with the barb 70 located behind the rear of the abdomen of the bee thus preventing the bee from leaving the chamber via the inlet. The tongue and barb thus function as a one-way valve, permitting entry of a bee to the chamber but preventing exit. Opening 56 is appropriately dimensioned to permit the head but not the body of the bee to pass therethrough, so the body of the bee is retained in the chamber. The barb 70 thus functions as retaining means. The chamber 88 is dimensioned to provide sufficient space for the bee to be accommodated therein, while preventing the bee from turning around or withdrawing its head into the chamber. The rib 51 assists in orienting the bee in the chamber, with the underside of the body of the bee being able to rest on the rib and the two rear pairs of legs of the bee possibly gripping the sides of the rib. The front pair of legs of the bee can pass through the openings 62, 64, further assisting in orienting the bee in the chamber. The wings of the bee are comfortably accommodated in the slightly wider upper region of the chamber 88.

Figure 14:
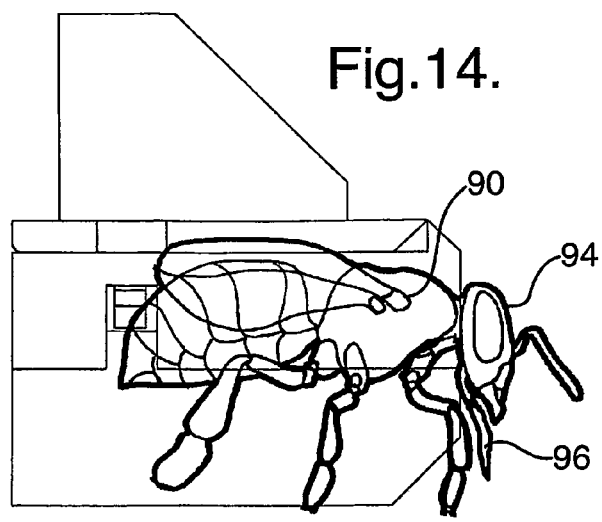
FIG. 14 is a side view of a bee in the bee holder of FIGS. 7 to 13, with the proboscis of the bee extended.

With the bee restrained in the holder, observations of the head can be made, particularly of extension of the proboscis 96, as illustrated in FIG. 14, with the slit 58 being positioned to facilitate proboscis extension outside the chamber and so facilitate monitoring thereof.

When observations have finished, the lid portion 44 may be pivoted away from the lower channel portion 42 around hinge 46, thus opening the chamber and permitting the bee to leave the chamber in undamaged and unharmed condition.

Figure 15:
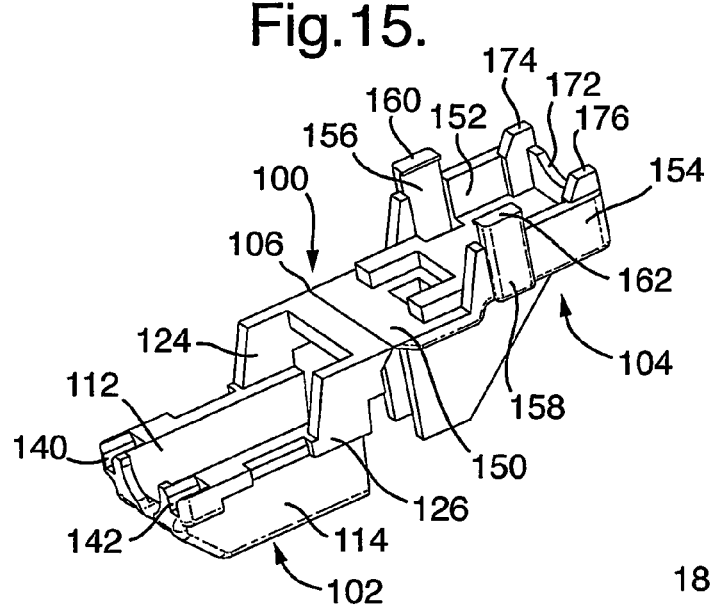
FIG. 15 is a view from the rear and to one side (the right side) of a moulding for a third embodiment of bee holder in accordance with the invention.
Figure 16:
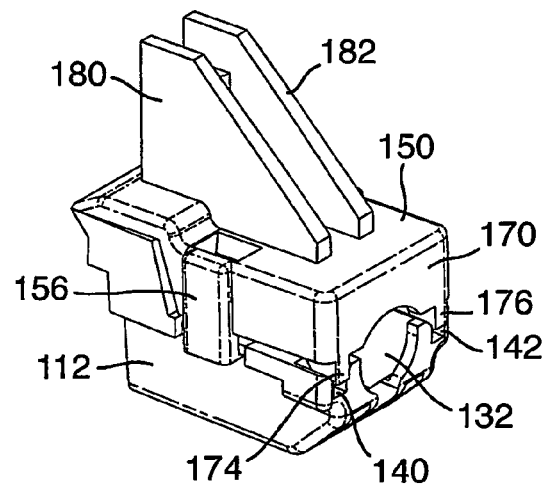
FIG. 16 is a view from the top and right side of the front of a bee holder formed from the moulding shown in FIG. 15, with the holder in a first, open position.
Figure 17:
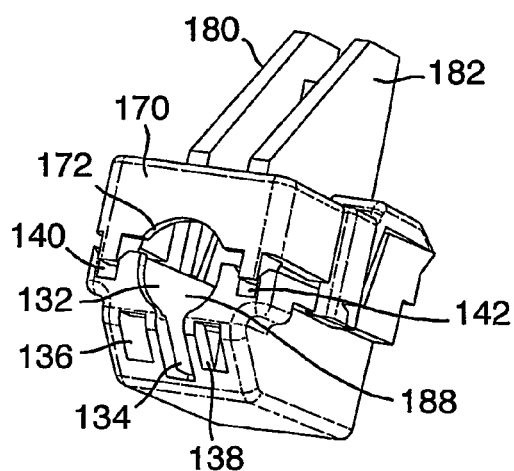
FIG. 17 is a view from below and the left side of the front of the bee holder shown in FIG. 16, in the first, open position.

FIGS. 15 to 30 illustrate another embodiment of bee holder having certain similarities to the holder of FIGS. 4 to 14. FIGS. 21, 22 and 27 to 30 include a schematic representation of a bee in the holder. The holder of FIGS. 15 to 30 is similarly made from a one piece polypropylene moulding 100 as shown in FIG. 15. The moulding comprises a lower channel portion 102 and an upper channel portion 104 connected by a thin web 106 (shown schematically in FIG. 15) that constitutes an integral "living" hinge. The two channel portions are pivoted together by nearly 180°, to produce the holder in a first, open position, as shown in FIGS. 16 to 20, defining a chamber 108. In this embodiment, the hinge is positioned at the rear of the holder in contrast to the previous embodiment in which the hinge is positioned at the front of the holder.

The lower channel portion 102 includes a bottom wall 110 with a longitudinal rib 111, and generally parallel side walls 112 and 114. The side walls include respective outwardly extending flange portions 120 and 122 that form part of a first latching mechanism, to be discussed below, for retaining the housing in the first position. The rear portions of the side walls include respective extensions 124 and 126 leading to the hinge formed by web 106. The rear of the lower channel portion is open. The lower channel portion includes a inclined front wall 130 that includes a part-circular opening 132 with a centrally located slit 134 extending downwardly therefrom. A respective aperture 136, 138 is located on each side of the slit 134. The front wall 130 also includes two recesses 140 and 142 forming part of a second latching mechanism, for securing the housing in a second, closed position to be discussed below.

Figure 19:
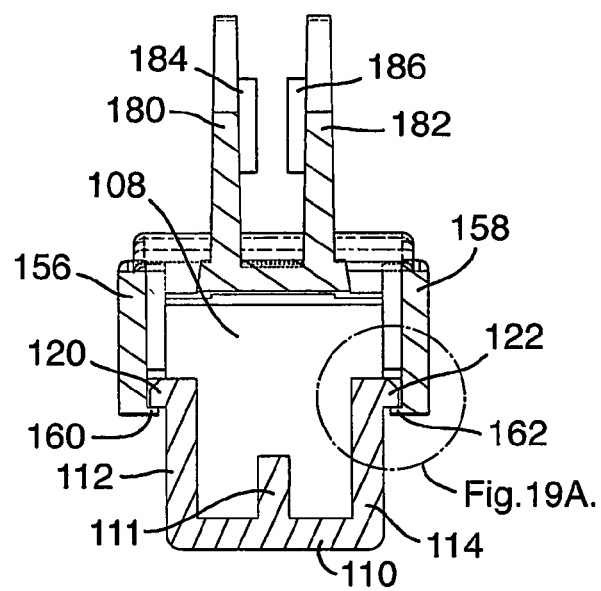
FIG. 19 is a sectional view along line B—B in FIG. 18.
Figure 19A:
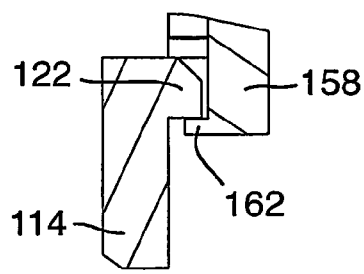
FIG. 19A is a detail of FIG. 19 on an enlarged scale.

The upper channel portion 104 includes a top wall 150 and two generally parallel side walls 152 and 154, the rear portions of these side walls being cut away to provide space to accommodate lower channel side wall extensions 124 and 126, respectively. The side walls include respective depending extensions 156 and 158 terminating in inwardly extending flange region 160 and 162 that co-operate with lower channel portion flanges 120 and 122, as shown in FIGS. 19 and 19A to provide a latching mechanism to retain the housing in the first position. The housing is of material that can deform to a necessary extent to permit latching engagement of the channel portions in this way on pivoting around the hinge 106. The hinge 106 also functions to provide a back torque retaining the moulding in this position.

The upper channel portion 104 includes a front wall 170 having a part circular opening 172 therein. The front wall 170 also includes a respective depending portion 174 and 176 on each side of opening 172 for engagement as a push fit in the recesses 140 and 142 in the lower channel portion front wall to secure the housing in the second, closed position, to be described below. In the first position these components are un-engaged.

The top wall 150 of the upper channel portion includes two generally triangular fins or mounting clips 180 and 182 extending upwardly therefrom. A respective location rib 184 and 186 extends inwardly from each fin.

Figure 18:
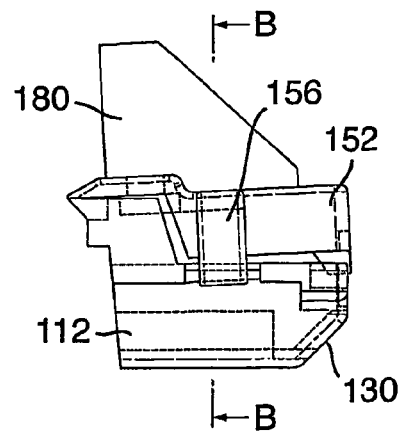
FIG. 18 is a view of the right side of the bee holder shown in FIGS. 16 and 17, in the first open position.

As noted above, in first, open position of the housing flange regions 160 and 162 of the upper channel portion engage with respective flange portions 120 and 122 of the lower channel portion, with the two channel portions not fully parallel but slightly inclined, as shown in FIG. 18. With the housing in this position, the openings 132 and 172 in the front walls together form a generally circular head opening 188 having a diameter of 4 mm, as seen best in FIG. 17.

The holder is of generally box-like form, having an overall length of 14.6 mm, an overall height of 9 mm (excluding the upstanding mounting clips which are 8 mm high), a maximum width of 9 mm, with a narrower lower portion 7 mm wide. The holder defines a generally box-like chamber 108 that is generally similar in size and configuration to that of the bee holder of FIGS. 7 to 14, having a width in the lower portion of 5 mm, with a wider upper portion. The open rear of the holder constitutes an inlet to the chamber and the circular opening 188 (which has a diameter of 4 mm) in the front wall constitutes a head opening for a bee located in the chamber. The chamber is dimensioned comfortably to accommodate the body of a bee with the head of the bee passing through opening 188.

Figure 20:
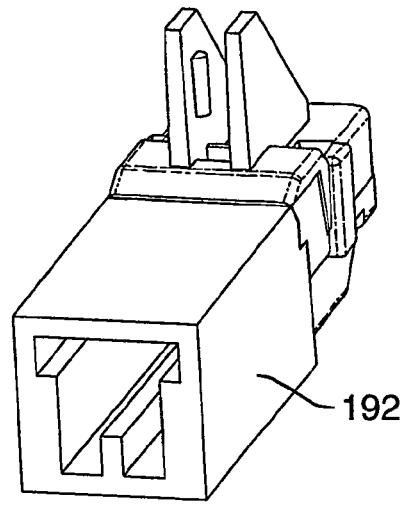
FIG. 20 is a view from the rear and right side of the bee holder shown in FIGS. 16 to 19 with an attached loading tunnel.
Figure 21:
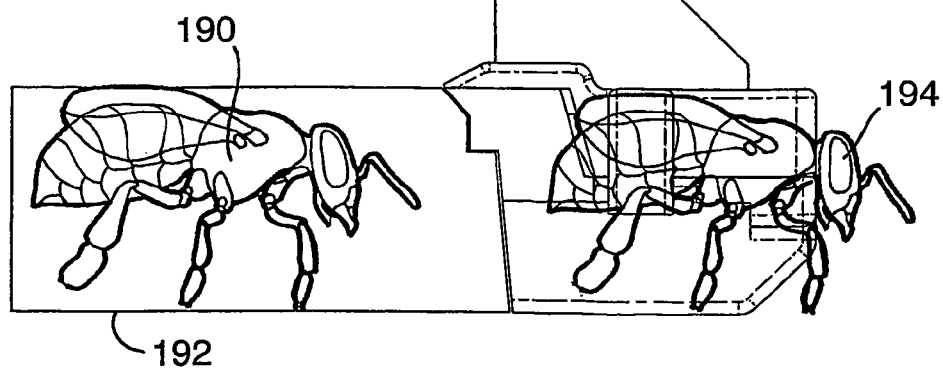
FIG. 21 is a schematic view of the right side of the bee holder and tunnel shown in FIG. 20.
Figure 23:
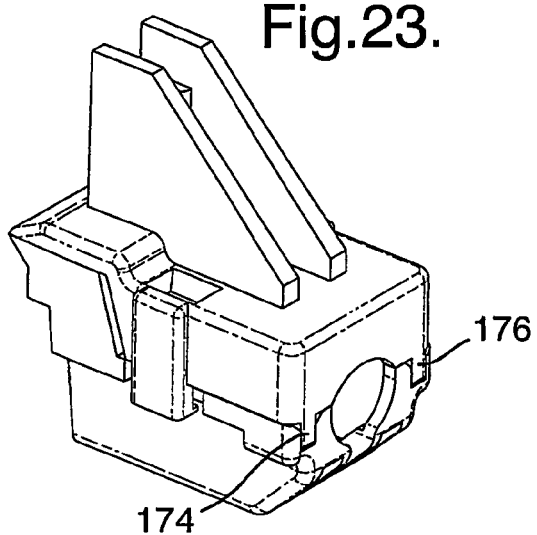
FIG. 23 is a view from the top and right of the front of the bee holder shown in FIGS. 16 to 22 in a second, closed position.
Figure 24:
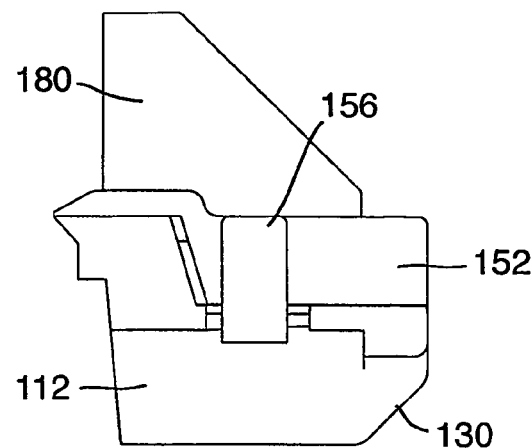
FIG. 24 is a view of the right side of the bee holder shown in FIGS. 16 to 23 in the second, closed position.

With the holder in the first, open position a bee can be located in the holder, entering through the open rear of the lower channel portion. A bee may be manually placed in the holder by a skilled handler. Alternatively, the bee 190 may be lured or encouraged to enter the holder, possibly via a loading tunnel 192 as shown in FIG. 20 and 21, e.g. being lured by an attractive scent, light etc.

Figure 22:
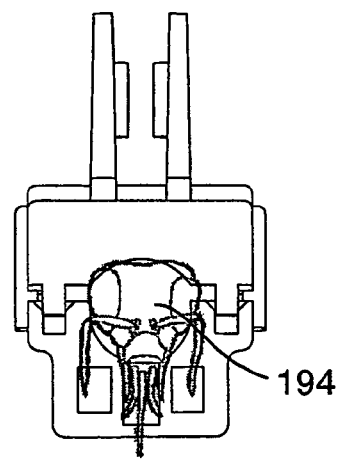
FIG. 22 is a front view of the bee holder shown in FIGS. 16 to 21, in the first open position, with a bee therein.
Figure 25:
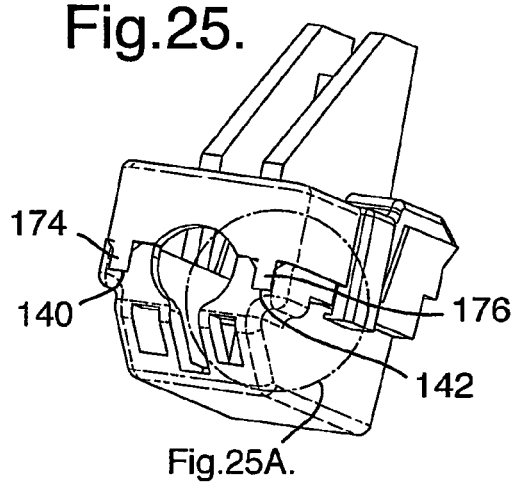
FIG. 25 is a view from the front and left side of the bee holder shown in FIGS. 16 to 24 in the second, closed position.
Figure 26:
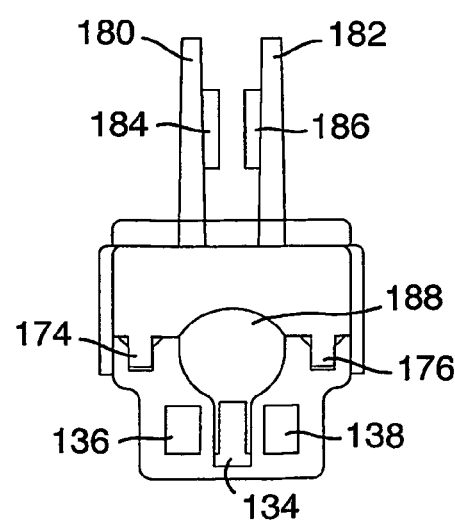
FIG. 26 is a front view of the bee holder of FIGS. 16 to 25 in the second, closed position.
Figure 25A:
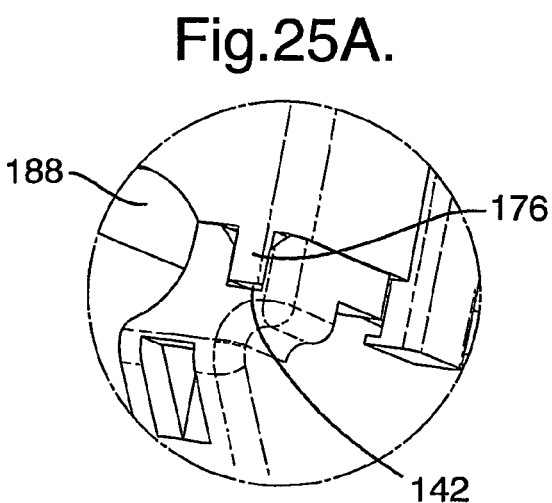
FIG. 25A is a detail of FIG. 25 on an enlarged scale.

When a bee is fully located in the chamber, with its head 194 protruding through opening 188, as shown in FIG. 22, the housing components can be moved to a second, closed positioned as shown particularly in FIGS. 22 to 25 by downwards force on the upper channel portion resulting in operation of the second latching mechanism by frictional engagement of portions 174 and 176 in recesses 140 and 142, as a push fit, as illustrated in FIG. 25. With the holder in the second position, the height of the head opening 188 is reduced to 3.6 mm which is too small to allow the bee to retract its head. The opening 188 thus functions as a collar that retains the bee in the holder, thus constituting retaining means.

Locking in this way may be achieved manually or automatically e.g. by a means of a powered actuator 200 such as a solenoid device operating in response to a photo diode 202 detecting the protruding head 194 of a bee interrupting light from a LED 204, as illustrated in FIG. 27.

FIGS. 28 to 30 illustrate a bee 190 in the housing in the second, closed position, with the bee able to pass its front legs to the exterior of the housing through openings 136 and 138. The lower part of the body of the bee rests on the rib 111, with the rear legs resting in cbannels formed on either side of the rib, as shown in FIG. 29. The under, upper part of the chamber provides space for the wings of the bee.

With the bee restrained in the holder, observations of the head can be made, particularly of extension of the proboscis 196, as illustrated in FIG. 30, with the slit 134 being positioned to facilitate proboscis extension outside the chamber and so facilitate monitoring thereof.

When observations have finished, the bee can be released from the holder by moving the holder back to the first, open position or by fully opening the holder. The bee is able to leave the chamber in undamaged, unharmed condition.

The invention claimed is:

1. An insect holder for holding an insect of a particular type, the holder comprising a housing with a chamber adapted to receive said insect, an inlet to the chamber through which said insect can pass to enter the chamber, a head opening to the chamber adapted to permit the head of said insect in the chamber to pass therethrough to the exterior of the housing while retaining the insect in the housing, and retaining means for retaining said insect in the chamber with the head of the insect protruding through the head opening to the exterior of the housing, such that the insect is unable to turn around in the chamber, wherein the retaining means comprise a collar or barb locatable between the head and thorax, between the thorax and abdomen or behind the abdomen of an insect in the chamber, and wherein the collar or barb is movable between an open position and a closed or latched position.

2. Apparatus according to claim 1, wherein the retaining means comprise closure means for closing the inlet.

3. Apparatus according to claim 1, wherein the head opening is circular or part circular.

4. Apparatus according to claim 1, wherein the head opening has a slit extending therefrom.

5. Apparatus according to claim 1, wherein the head opening has a head restraint associated therewith.

6. Apparatus according to claim 1, wherein the chamber has an internal longitudinal projection or rib running along at least part of the length thereof.

7. Apparatus according to claim 1, wherein the chamber includes apertures constituting leg holes through which the legs of an insect in the holder can pass.

8. Apparatus according to claim 1, adapted to hold a forager honey bee, wherein the chamber has a width of at least 5 mm and a length of about 13 mm, with the head opening being about 4 mm in diameter.

9. Apparatus according to claim 1, wherein the housing is made of rigid plastics material.

10. An insect holder in accordance with claim 1, with an insect, particularly a bee, held therein.

11. Odour sensing apparatus comprising an insect holder in accordance with claim 10; and means for detecting a response of the insect in the holder to an odour.

12. Apparatus according to claim 1, including activation means for moving the collar or barb.

13. Apparatus according to claim 12, wherein the activation means functions automatically to move the collar or barb in response to correct positioning of an insect in the holder.

14. An insect holder dimensioned to hold and restrain an individual bee, the holder comprising a housing with a chamber adapted to receive the bee, an inlet to the chamber through which the bee can pass to enter the chamber, a head opening to the chamber adapted to permit the head of the bee in the chamber to pass therethrough to the exterior of the housing while retaining the bee with respect to the housing, and retaining means for retaining the thorax and abdomen of the bee in the chamber with the head of the bee protruding through the head opening to the exterior of the housing, such that the bee is unable to turn around in the chamber or withdraw its head into the chamber, the protruding head of the bee being accessible for monitoring or observation of the behavior of the bee wherein the retaining means comprise a collar or barb locatable between the head and the thorax, between the thorax and abdomen or behind the abdomen of a bee in the chamber.

15. Apparatus according to claim 14, wherein the collar or barb is movable between an open position, in which movement of the bee into or out of the chamber is permitted, and a closed or latched position in which movement of the bee from the chamber is prevented.

16. Apparatus according to claim 15, including activation means for moving the collar or barb.

17. Apparatus according to claim 16, wherein the activation means functions automatically to move the collar or barb in response to correct positioning of the bee in the holder.

18. A method of monitoring or observing the behavior of an insect, the method comprising causing or allowing the insect to enter, head first, an inlet at one end of a chamber of a holder, causing or allowing the insect to proceed into the chamber, which is sufficiently confined to oblige the insect to proceed head first, until the head of the insect protrudes through a head opening at the other end of the chamber, restraining the insect such that the insect is unable to turn around in the chamber or withdraw its head into the chamber, thereby rendering the head of the insect accessible for monitoring or observing the behavior of the insect, and removing the restraint in order to release the insect unharmed.

* * * * *

UNITED STATES PATENT AND TRADEMARK OFFICE
CERTIFICATE OF CORRECTION

PATENT NO. : 7,036,454 B2 Page 1 of 1
APPLICATION NO. : 10/497605
DATED : May 2, 2006
INVENTOR(S) : Paul James Davis et al.

It is certified that error appears in the above-identified patent and that said Letters Patent is hereby corrected as shown below:

On the title page: (Item 73):
Please correct the assignee's name to read: Inscentinel Ltd.

Signed and Sealed this

Second Day of January, 2007

JON W. DUDAS
*Director of the United States Patent and Trademark Office*